United States Patent [19]

Cambiaghi et al.

[11] Patent Number: 5,424,196
[45] Date of Patent: Jun. 13, 1995

[54] ENZYMATIC PROCESS FOR PREPARING 7-AMINOCEPHALOSPORANIC ACID AND DERIVATIVES

[75] Inventors: Stefano Cambiaghi, Pavia; Sergio Tomaselli, Milan; Roberto Verga, Cassano D'Adda, all of Italy

[73] Assignee: Antibioticos S.p.A., Milan, Italy

[21] Appl. No.: 176,520

[22] Filed: Jan. 3, 1994

Related U.S. Application Data

[63] Continuation of Ser. No. 810,281, Dec. 19, 1991, abandoned.

[30] Foreign Application Priority Data

Dec. 21, 1990 [IT] Italy .................. 22514REG.A

[51] Int. Cl.$^6$ ............................................. C12P 35/02
[52] U.S. Cl. .......................................... 435/51; 435/47; 435/174; 435/189; 435/69.1; 435/190
[58] Field of Search ...................... 435/51, 47, 49, 174, 435/175, 176, 177, 189, 190, 69.1, 172.1, 240.1, 320.1, 230

[56] References Cited

U.S. PATENT DOCUMENTS

| | | | |
|---|---|---|---|
| 3,658,649 | 4/1972 | Arnold et al. | 435/191 |
| 3,801,458 | 4/1974 | Fildes et al. | 435/184 |
| 3,960,662 | 6/1976 | Matsuda et al. | 435/182 |
| 4,075,061 | 2/1978 | Fleming et al. | 435/47 |
| 4,170,696 | 10/1979 | Hirohara et al. | 435/180 |
| 4,195,129 | 3/1980 | Fukui et al. | 435/182 |
| 4,272,617 | 6/1981 | Kaetsu et al. | 435/182 |
| 4,371,612 | 2/1983 | Matsumoto et al. | 435/181 |
| 4,414,328 | 11/1983 | Imanaka et al. | 435/47 |
| 4,533,632 | 8/1985 | Smith et al. | 435/47 |
| 4,693,977 | 9/1987 | Wolfe et al. | 435/47 |
| 4,745,061 | 5/1988 | Aretz et al. | 435/47 |
| 4,774,178 | 9/1988 | Ichikawa et al. | 435/51 |
| 4,912,038 | 3/1990 | Schilling, Jr. et al. | 435/69.1 |
| 4,990,444 | 2/1991 | Aretz et al. | 435/253.3 |
| 5,104,800 | 4/1992 | Crawford et al. | 435/47 |

FOREIGN PATENT DOCUMENTS

| | | |
|---|---|---|
| 322032 | 6/1984 | European Pat. Off. |
| 63-74488 | 4/1988 | Japan |
| 9012110 | 10/1990 | WIPO |

OTHER PUBLICATIONS

Komatsu et al. (1989) Chem. Abstr. vol. 110, p. 557, abs. #110:113193y.
Sofer et al. (1983) Biotechniques 1(4):198–203.
Simonetta et al. (1989) Eur. J. Biochem. 180:199–204.
Simonetta et al. (1987) Biochim. Biophys. Acta 914:136–142.
Matsuda et al. (1985) J. Bacteriology 163(3):1222–1228.
Matsuda et al. (1987) J. Bacteriology 169(12):5815–5820.
Naoi et al. (1978) Biochim. Biophys. Acta 523:19–26.
Carrea et al. (1983) Biochim. Biophys. Acta 745:181–188.
Massey et al. (1979) Anal. Biochem. 95:156–159.
Lemainque et al. (1988) Eur. J. Biochem. 174:171–176.
Parkin et al. (1979) Biotech. Bioeng. 21:939–953.
Garcia, Jose L., et al., "An Improved Method to Clone Penicillin Acylase Genes: Cloning and Expression in *Escherichia coli* of Penicillin G Acylate from *Kluyvera citrophila*", J. of Biotech., pp. 187–195 (1985).
Forney, Larry J., et al., "Selection of Amidases with Novel Substrate Specifications from Penicillin Amidase of *Escherichia Coli*", Applied and Environmental Microbiology, vol. 55 (No. 10) pp. 2550–2555, (1989).
Shubuya, Yuzo, et al., "Isolation and Properties of 7β-(-4-Carboxybutanamido)cephalosporanic Acid (List continued on next page.)

*Primary Examiner*—Charles L. Patternson, Jr.
*Attorney, Agent, or Firm*—Stevens, Davis, Miller & Mosher

[57] ABSTRACT

Transformation of Cephalosporin C or its derivatives and salts into 7-aminocephalosporanic acid or its derivatives by an enzymatic two stage process with enzymes immobilized on a solid matrix.

11 Claims, 6 Drawing Sheets

Amp<sup>r</sup> : Ampicillin
Cam<sup>r</sup> : Chloramphenicol
gla : Glutaryl-7-ACA acylase
tac<sup>P</sup> : tac promoter
Tet<sup>r</sup> : Tetracycline
galK : Galactokinase

ENZYMATIC PROCESS FOR PREPARING 7-AMINOCEPHALOSPORANIC ACID AND DERIVATIVES

This application is a Continuation of application Ser. No. 07/810,281, filed Dec. 19, 1991, now abandoned.

FIELD OF THE INVENTION

This invention relates to a process for the enzymatic production of 7-aminocephalosporanic acids or derivatives from Cephalosporin C or its derivatives. More particularly, the process relates to the transformation of Cephalosporin C or its derivatives and salts into 7-aminocephalosporanic acid or its derivatives by a two stage enzymatic process with enzymes immobilized on a solid matrix. 7-aminocephalosporanic acid (7-ACA) is a known important intermediate in the production of antibiotics of the Cephalosporin family.

The conversion of Cephalosporin C into 7-ACA has been known for some time and can be effected either by a chemical hydrolysis process (see Belgian patent 615955) or by an enzymatic process. The chemical process involves the use of very toxic and pollutant reactants (chlorinated solvents, chlorosilanes, dimethylaniline) and severe operating conditions (very low temperatures such as $-50°$ C.).

Known enzymatic processes can be divided into two groups, namely those in which the operation is conducted in a single stage using an enzyme in the form of an acylase active on Cephalosporin C, obtained for example from a Pseudomonas culture (EP 275901), and those conducted in two stages.

In this latter method the first stage involves the enzymatic conversion of Cephalosporin C into glutaryl-7-aminocephalosporanic acid using D-amino acid oxidase (DAO; EC-1.4.3.3) obtained from cultures of various microorganisms such as *Trigonopsis variabilis*, Aspergillus, Penicillium, Neurospora, Pseudomonas, Cephalosporium. as described in the patents BE 736934, DT 2219454, FR 2133927, JP 52.125696 and JP 52.128295.

In the second stage, the aforesaid glutaryl derivative is hydrolyzed to 7-ACA using a specific acylase obtained from Comamonas, Pseudomonas (GB 1490634) or Arthrobacter (JP 52.1282293) bacterial cultures.

The process according to the present invention represents innovative technical progress over known two-stage processes by virtue of the considerable yields obtained. This advantage is obtained by adopting particular expedients and operating conditions and by the use of highly selective enzymes purified and immobilized on solid matrices insoluble in the reaction medium. The process can be represented as follows:

First stage:

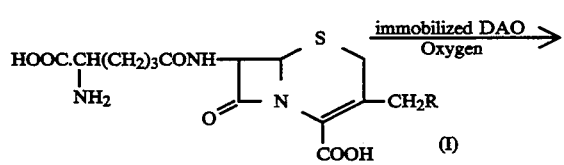

(I)

-continued

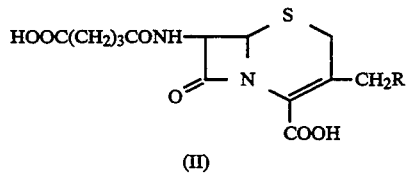

(II)

Second stage:

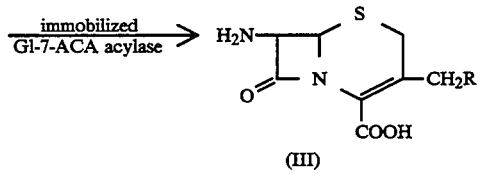

(III)

where R is $-OCOCH_3$, $-H$, $-OH$, $-OCONH_2$.

PROCESS OF THE INVENTION

Figure 1:
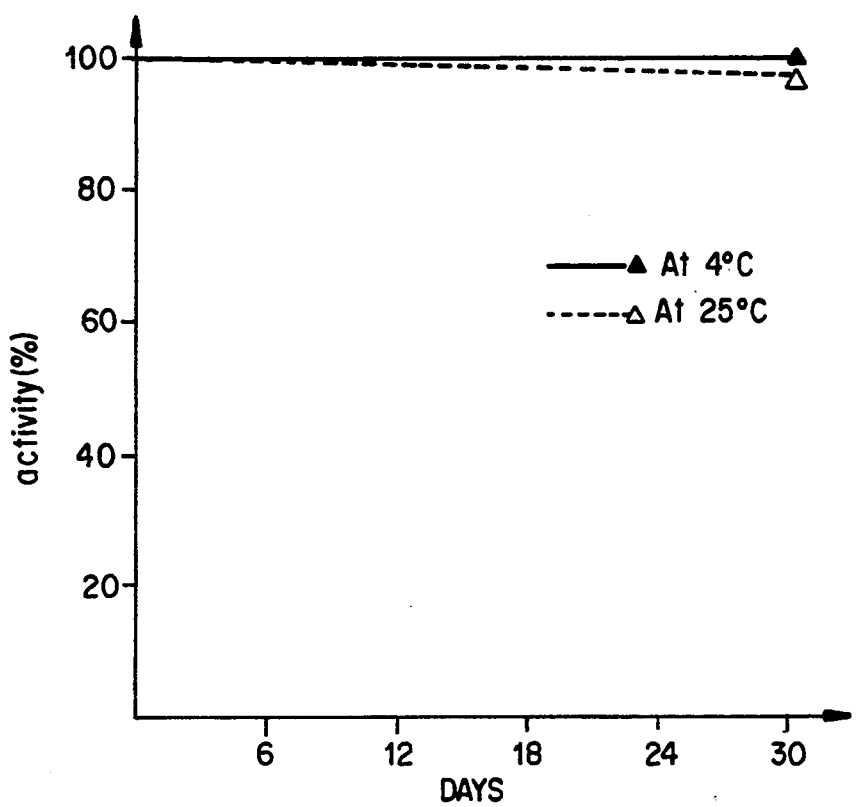
FIG. 1 is a graph of the stability of immobilized DAO over time.

According to the present invention the enzymatic conversion does not use enzymes in the form of a cell mass or aqueous solution, but instead said enzymes are transformed into an immobilized solid form insoluble in an aqueous medium, which is particularly suitable for the industrial conversion of Cephalosporin C into 7-aminocephalosporanic acid ($R=-OCOCH_3$).

Because of their insolubility in the reaction medium, these immobilized enzymes have the advantage of being easily recoverable from the reaction medium and usable a large number of times, this being a necessary and indispensable condition for an industrial process.

A further important industrial advantage of the present invention is the fact that the ease of recovery of the enzyme from the reaction mass not only simplifies the recovery of the final product but also enables the reaction solution obtained in the first stage to be used directly in the second stage. These advantages therefore enable the process to be conducted continuously with a single liquid stream from one enzymatic stage to the other.

FIRST STAGE: OXIDATIVE DEAMINATION TO GLUTARYL DERIVATIVE

The first process stage in the conversion of the cephalosporanic compound (I) according to the present invention is based on the use of a particularly specific D-amino acid oxidase (DAO) for the oxidative deamination reaction on the D-aminoadipic chain.

The enzyme used in the process of the invention is obtained from *Rhodotorula gracilis* ATCC 26217 cultures.

The enzyme is isolated from the culture obtained by fermentation, purified of interfering enzymes and subjected to an immobilization process to obtain a form insoluble in an aqueous medium and to increase its stability.

The enzymatic conversion of the compound (I) into the glutaryl derivative (II) is conducted in aqueous solution maintaining a suitable pH value by adding basic reagents.

The pH can vary from 7 to 8.5. However because of the instability of cephalosporanic compounds in an alkaline environment it is preferable to operate at pH 7.5. The reaction temperature can vary from 20° to 30° C., and is normally 25° C.

The enzymatic conversion must be effected in the presence of air or oxygen by blowing these gases into the aqueous solution. The gas flow can vary from 0.5 to 1 volume/volume of solution/minute.

The concentration of the initial substrate (I) can vary from 20 to 100 g/l. In the particular case of Cephalosporin C its crystallized sodium or potassium salt can be used, or alternatively direct use can be made of their purified solutions as obtained from the recovery of the fermentation broths before the final crystallization step.

The immobilized enzyme according to the present invention is used in fine granular form and is maintained in suspension by mechanical stirring or with the aid of the air or oxygen flow. Alternatively the conversion can be effected by a continuous process by loading the immobilized enzyme into a percolation column and passing through it the substrate solution kept saturated with oxygen at a constant pH of 7.5.

The time required for complete transformation is of the order of 0.5-3 hours depending on the operating conditions. The conversion yield to the glutaryl derivative is high, and normally around 90%. At the end of the reaction the product still contains some 5-ketoadipyl-7-aminocephalosporanic acid (IV):

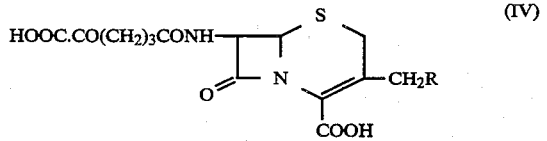

(IV)

which has not converted into the desired glutaryl derivative (II), where R is —OCOCH$_3$, —H, —OH, —O-CONH$_2$.

According to the present invention, this ketoadipyl derivative (IV) can be further converted into glutaryl derivative (II) by adding to the aqueous reaction solution, after separating the immobilized DAO enzyme, a quantity of H$_2$O$_2$ stoichiometric with respect to the compound to be transformed, and allowing them to react at a temperature of 20°-25° C. for a time of between 10 and 15 minutes. An excess of H$_2$O$_2$ can be used in order to reduce the reaction time.

The excess H$_2$O$_2$ is then eliminated before passing to the next stage by means of a suitable reducing agent such as pyruvic acid or its salts or alkaline sulphites.

This practically complete elimination of the said compound (IV) not only results in a final glutaryl derivative yield of around 95% but represents a great advantage for the subsequent enzymatic hydrolysis step. In this respect, hydrolysis with Gl-7-ACA acylase is specific for the glutaryl derivatives and does not recognise the ketoadipyl derivatives (IV), which then remain as undesirable impurities in the final product.

As already stated, an aspect of the invention is the use of a DAO enzyme produced from *Rhodotorula gracilis* ATCC 26217. This is an FAD dependent enzyme (flavoprotein) of endocellular nature, as is that obtainable from *Trigonopsis variabilis*, the source most cited in the technical literature. DAO produced from *Rhodotorula gracilis* is however characterised by a more stable bond with the FAD, as is apparent from the low dissociation constant, ie $2.2 \times 10^{-8}$ M.

DAO produced from *Rhodotorula gracilis* differs considerably not only in the physico-chemical properties of the enzymatic protein but also in the set of inhibitors and the specificity on D-amino acids taken as substrate [Pilone Simonetta M. et al., Eur. J. Biochem. 180, 199 (1989); Kubicek-Pranz E. M. et al., J. of Appl. Biochem. 7, 104 (1985)].

In particular, DAO from *Rhodotorula gracilis* has excellent specificity for Cephalosporin C with Km and Vmax values very similar to those encountered for D-alanine, which is the specific substrate for this enzyme.

The present invention enables the D-amino acid oxidase enzyme to be obtained from *Rhodotorula gracilis* cultures by a simple column fractionation method in purified form and practically free of catalase, esterase and β-lactamase, ie the enzymes normally present in crude DAO solutions and which interfere in the enzymatic transformation of Cephalosporin C into glutaryl-7-aminocephalosporanic acids in that:

catalase destroys the H$_2$O$_2$, with consequent blockage of decarboxylation and stoppage of the reaction to ketoadipyl derivatives;

esterase, in compounds of type (I) in which R=O-COCH$_3$, leads to the formation of undesirable desacetyl derivatives;

β-lactamase hydrolyzes the β-lactam ring with destruction of the cephalosporanic structure.

The DAO solutions obtained in this manner are therefore valid in terms of purity and catalytic functionality, but as in the case of all DAOs in solution are not very stable, and in this form have little industrial interest. The immobilized forms obtained according to the invention have however very high stability and are industrially valid for the production of glutaryl-7-aminocephalosporanic acids.

Figure 2:
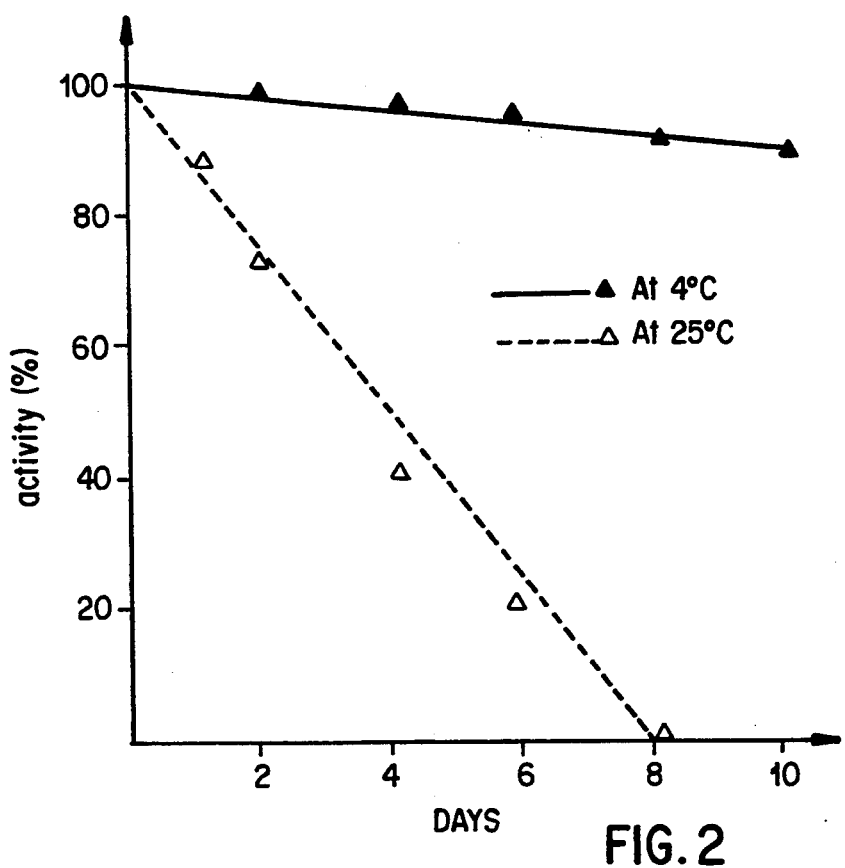
FIG. 2 is a graph of the stability of DAO in aqueous solution over time.

In this respect reference should be made to the stability diagram for immobilized DAO in FIG. 1 compared with that of FIG. 2 for the enzyme in aqueous solution.

In addition, the immobilized DAO according to the invention maintains high activity under the operating conditions of the process of oxidative deamination of Cephalosporin C or its derivatives for a very long period and therefore for a large number of operations. In this respect reference should be made to the diagram of FIG. 3 which shows the activity (in percentage of initial activity) against the hours of use in the enzymatic process at 25° C. and pH 7.5.

The use of the DAO enzyme obtained from *Rhodotorula gracilis* in purified form according to the present invention is therefore fundamental in obtaining glutaryl-7-aminocephalosporanic acid solutions particularly suitable for use as such without further purification, in the subsequent enzymatic process in the presence of acylase.

The preparation of the immobilized enzyme required for the first stage of the present invention is essentially based on the following operating steps:

1 fermentation to produce Rhodotorula gracilis ATCC 26217 cells;
2 extraction and purification of the D-amino acid oxidase enzyme from the Rhodotorula gracilis cells;
3 immobilization of the D-amino acid oxidase on water-insoluble solid matrices;

1 Fermentation of Rhodotorula gracilis ATCC 26217

The Rhodotorula gracilis is cultivated by aerobic fermentation. The culture broth components are those generally used for yeast production using nitrogen sources such as D and DL amino acids, peptones, yeast extracts, corn steep liquor etc; carbon sources such as glucose, saccharose, maltose and beet and sugar cane molasses; and mineral salts such as sodium chloride, calcium chloride, zinc sulphate, magnesium sulphate etc. A particularly suitable culture broth for the production of Rhodotorula gracilis cells of high DAO enzyme content has the following composition limits:

| | |
|---|---|
| NaCl | 0.5–1 g/l |
| $K_2HPO_4$ | 1–2 g/l |
| $MgSO_4$ | 0.5–1 g/l |
| $CaCl_2$ | 0.2–0.3 g/l |
| $ZnSO_4$ | 0.001–0.002 g/l |
| $FeCl_3$ | 0.002–0.003 g/l |
| Corn steep liquor | 0.5–1 g/l |
| Glucose (or maltose) | 20–30 g/l |
| D-alanine (or DL-alanine) | 4–8 g/l |

Fermentation is effected after sterilizing the broth at 120° C. and cooling to 30° C., after which the inoculum in the form of a vegetative culture of Rhodotorula gracilis is introduced. The culture is kept stirring at 24°–32° C., and aerated by balanced blowing of air at a rate of 0.5–1 volumes/volume of broth/minute. The pH of the medium is maintained between 4 and 6.5, preferably 5, by adding non-nitrogenated bases. The duration of fermentation can vary from 24 to 48 hours depending on the operating conditions such as composition of the culture medium, stirring, temperature.

2 Extraction and purification

D-amino acid oxidase obtained from Rhodotorula gracilis is an endocellular enzyme.

On termination of fermentation the culture broth is therefore centrifuged to separate and recover the corpusculate.

The cell paste is resuspended in water, raised to pH 6–9 (preferably 8) by adding NaOH and subjected to lysis using physical means (sonication) or to chemical treatment (addition of surfactants and water-immiscible solvents).

A preferred method is to resuspend the cell paste in a medium buffered at pH 8 (preferably phosphate buffer with the addition of small quantities of alkaline bisulphite and a cationic surfactant such as cetylpyridinium chloride) and subjecting the suspension to multiple passage through a press at 550 bars or through a ball mill.

The cell lysate is then flocculated, clarified by centrifuging, concentrated by ultrafiltration and salted by adding ammonium sulphate. The salted precipitate, which contains D-amino acid oxidase, is separated by filtration and resuspended in buffer solution at pH 8.

In this manner a solution is obtained consisting of crude enzyme accompanied by small quantities of the interfering enzymes, ie catalase, esterase and $\beta$-lactamase. The crude enzyme is then purified by known methods.

A preferred method for purifying the enzyme obtained in this manner is chromatographic fractionation in a column with ion exchange resin having the diethylaminoethyl (DEAE) group as its ionizable function, such as Sepharose ® (Pharmacia), Trisacryl ® (IBF), Toyopearl ® (Toso Haas), with 25 mM phosphate buffer of pH 8.

The interfering enzymes, in particular the esterase, are retained by the column resin while the thus purified DAO passes directly into the percolate.

In this manner an enzyme is obtained with a specific activity of 15–20 U/mg of protein and free of undesired catalytic activity. The thus purified DAO is stable for 6 days at 4° C. and for at least 6 months at −20° C., and can be used directly in the immobilization process.

3 Immobilization of D-amino acid oxidase

The method according to the present invention consists of immobilizing the D-amino acid oxidase on solid supports, generally commercial ion exchange resins.

The immobilization of enzymes on ion exchange resins has been long known but has never been described of studied for DAO produced from Rhodotorula gracilis.

The following are used as matrices in the present invention:

strongly basic resins of macroreticular polystyrene structure with a quaternary amine function, such as Amberlite IRA 900 (Röhm and Haas);

weakly basic resins of macroreticular polystyrene structure with a primary amino Function such as Duolite A 365 (Röhm and Haas);

medium basicity resins of polycondensed phenol-formaldehyde structure with secondary and tertiary amine functional groups such as Duolite A 568 or Duolite A 7 (Röhm and Haas).

According to the present invention said types of resin are buffered at pH 6–9, preferably pH 8, with 0.1M phosphate buffer. A solution of a bifunctional agent able to form cross-linkages between the enzymatic protein and the functionalized matrix is added to the buffered resin. Suitable bifunctional agents are aliphatic dialdehydes such as glutaraldehyde and malonaldehyde. Normally a solution of glutaraldehyde in phosphate buffer of pH 7–9, generally 8, is used at a concentration of 1–4%, generally 2%. After 15–60 minutes at a temperature of between 4° C. and 30° C., preferably 30 minutes at 20° C., the supernatant is separated by decantation and the DAO enzyme solution at a pH of 6–9, preferably 8, in 25 mM phosphate buffer is added to the wet resin. After contact for 2–24 hours at a temperature of 4–20° C., normally 12 hours at 4° C., the resin with the immobilized enzyme is separated by filtration.

The present invention also relates to the immobilization of DAO on:

matrices of polyacrylic structure and in particular with epoxide terminal groups such as Eupergit C ® (Röhm-Pharma);

inorganic matrices such as porous alumina impregnated with a complex of polyethylenimine and glutaraldehyde such as UOP IPS-200 ® (UOP-USA).

Table 1 shows the characteristics of the matrices used according to the present invention, the bonding capacity and the activity of the immobilized DAO.

For each matrix three immobilization tests are shown, conducted with increasing quantities of enzyme to attain complete saturation of the support. With the support saturated the best activity after binding is of the order of 50–75 U/g wet.

Normally 200 U are bound per gram of wet support so that attachment is complete, the activity after binding being around 40–50 U/g wet and the functionality, in terms of activity of the immobilized enzyme as a percentage of the activity of the corresponding free enzyme, being 20–30%.

Figure 3:
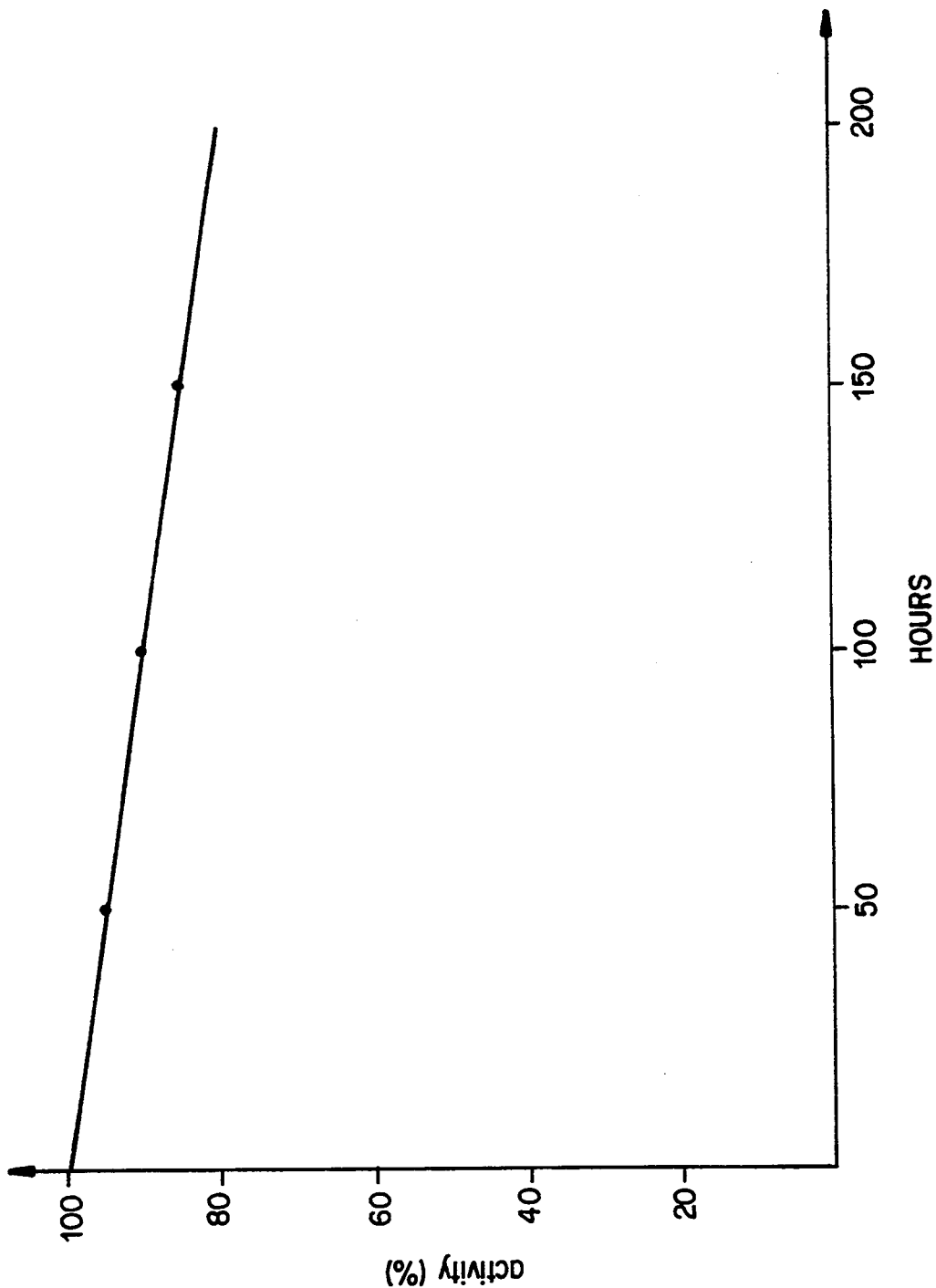
FIG. 3 is a graph showing the stability of immobilized DAO during the enzymatic process of convening cephalosporanic compounds into glutaryl derivatives.

The great advantage of immobilized DAO is its stability, which allows it to be used for mope than 200 hours in converting cephalosporanic compounds of type (I) into glutaryl derivatives (II) in the enzymatic process at 25° C., pH 7.5 (see FIG. 3).

Measurement of D-amino acid oxidase (DAO) activity

The activity of the D-amino acid oxidase enzyme is evaluated by measuring the $H_2O_2$ quantity evolved on reacting the enzyme on a substrate of D-alanine in 100 mM phosphate buffer at pH 7.5 saturated with oxygen at 37° C.

The $H_2O_2$ is determined kinetically using a peroxidase-based reactant, 4-aminophenazone and 2,4-dichlorophenolsulphonate by the modified Trinder reaction (J. Clin. Path. 22, 246, 1969). The red colour which forms (quinonimine) is proportional to the hydrogen peroxide evolved in the test and is measured spectrophotometrically at 510 nm.

One unit of D-amino acid oxidase is that quantity of enzyme (free or immobilized) which under the conditions used in the method produces one $\mu$mole of $H_2O_2$ per minute.

Protein measurement

The protein content of the enzymatic solutions is measured spectrophotometrically by the Bradford method (Anal. Biochem. 72, 248, 1976) using Coomassie Brilliant Blue G250 against the standard bovine albumin curve.

SECOND STAGE: DEACYLATION OF THE GLUTARYL DERIVATIVE

The second stage in the process of converting Cephalosporin C or its derivatives and salts into 7-aminocephalosporanic acid or derivatives is based on the use of a specific immobilized acylase to catalyze the deacylation of the glutaryl derivative (II). This enzyme, known hereinafter as Gl-7-ACA acylase (glutaryl-7-ACA acylase) is produced from cultures of genetically engineered microorganisms obtained from non-$\beta$-lactamase producing *Escherichia coli* collection strains in which the gene of Gl-7-ACA acylase isolated from any microorganism of the Acinetobacter species, the producer of this enzyme, has been cloned.

The preparation of these microorganisms by the recombinant DNA technique is the subject of Spanish patent application No. 9002109 of 3 Aug. 1990 in the name of Antibioticos S.A., an associate of the applicant of the present patent application, Antibioticos S.p.A.

Microorganisms which are particularly suitable for the production of Gl-7-ACA acylase are: *E. Coli* ATCC 9637 (p JC 200) and *E. Coli* P-3 (p JC 200) reg No. NCIMB 40433, descendants respectively of the *E. Coli* ATCC 9637 and *E. Coli* P-3 reg. NCIMB No. 40432, in which the Gl-7-ACA acylase gene obtained for example from the microorganism Acinetobacter ATCC 53891, the producer of this enzyme, has been cloned.

Optimization of the fermentation conditions with this microorganism has enabled high productivity of Gl-7-ACA acylase without $\beta$-lactamase and only small quantities of esterase to be obtained.

With the present invention the Gl-7-ACA acylase is purified of the esterase by column chromatography, the purified enzyme being immobilized on solid matrices.

The enzymatic reaction can be schematically represented as follows:

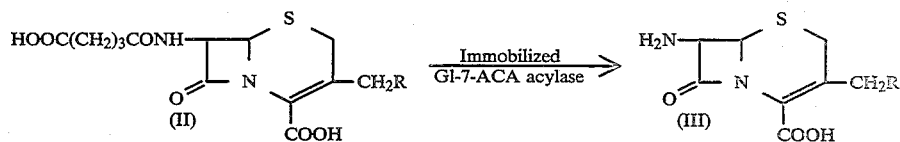

where R is $-OCOCH_3$, $-H$, $-OH$, $-OCONH_2$.

In this second stage the aqueous solution of glutaryl derivative (II) obtained in the first stage is used directly as substrate in this second stage as it does not require any preliminary purification given the high selectivity in the first conversion stage.

The concentration of glutaryl derivative (II) in the solution can vary from 10 to 30 g/l.

The enzymatic conversion is conducted by bringing the solution of glutaryl derivative (II) into contact with the Gl-7-ACA acylase enzyme immobilized on the solid support, operating at a temperature between 20° and 35° C. During the operation the pH of the glutaryl derivative solution is maintained between 7 and 9, preferably around 8, by adding inorganic or organic bases such as ammonium hydroxide, alkaline hydroxides, aliphatic amines such as triethylamine or buffer solutions of alkaline phosphate type. The conversion duration can vary from 30 to 120 minutes depending on the operating conditions.

The enzymatic conversion can be conducted discontinuously by maintaining the immobilized enzyme dispersed in the solution of glutaryl derivative (II).

A preferred method is to load the supported enzyme into a column (or several columns operating in series) and pass the substrate solution continuously through them.

The 7-aminocephalosporanic acid or its derivatives is separated from the reaction solution obtained by crystallization, after acidifying to pH 3–3.5, depending on the isoelectric point of the final product, with inorganic acids such as hydrochloric, sulphuric or phosphoric acid.

An important innovation over the known art is that said enzyme, besides being obtained in very pure form, is not used in the form of a cell mass or aqueous solution, but is transformed into an immobilized solid form insoluble in an aqueous environment which is particularly suitable for the industrial conversion of glutaryl-7-aminocephalosporanic acid into 7-ACA.

Because of its insolubility in the reaction medium, this immobilized enzyme has the advantage of being easily recoverable from the reaction medium and usable a large number of times, this being a necessary and indispensable condition for an industrial process.

All these advantages make it possible to conduct the process either operating batchwise in a stirred reactor with the enzyme maintained in suspension, or operating with fixed bed columns through which the glutaryl-7-aminocephalosporanic acid obtained directly in the first stage is passed continuously.

A further important industrial advantage of the present invention is the fact that the ease of separation of the enzyme from the reaction mass also simplifies the recovery of the final product.

Further important advantages obtained using the immobilized Gl-7-ACA acylase according to the present invention are the following:

the high selectivity of the immobilized enzyme leads to high conversions and yields, generally of the order of 80–90%, resulting in a final product of high purity and thus not requiring laborious purification procedures;

in contrast to enzymes in the form of a cell paste or aqueous solution, the immobilized enzyme because of its insolubility does not release impurities into the reaction medium which could result in coloration or a lowering in purity of the final product.

The preparation of the Gl-7-ACA acylase in accordance with the invention, using cultures of microorganisms obtained by the recombinant DNA technique, comprises the following operational steps.

1) Cloning the gene for Gl-7-ACA acylase in non-β-lactamase producing *E. coli*, in accordance with the following conventional scheme:
   a) preparing plasmids;
   b) preparing the DNA donor containing the genetic information relative to the production of Gl-7-ACA acylase;
   c) inserting the DNA donor fragments into the plasmids of point a);
   d) selecting the carrier plasmids for the Gl-7-ACA acylase gene;
   e) constructing the final vector;
   f) transforming the non-β-lactamase producing *E. coli* strains with the vector of point e).

2) Fermentation of the microorganism obtained in 1)

The cloned *E. coli* is cultivated by aerobic fermentation. The medium is prepared using carbon sources such as glucose, saccharose, starch etc.; nitrogen sources such as amino acids, protein hydrolyzates, yeast extracts, corn steep liquor, soya meal; and mineral salts such as sodium chloride, potassium phosphates etc.

Fermentation is effected after sterilizing the broth at 120° C. and cooling to 21°–28° C., after which chloramphenicol is sterilely introduced at 30 mg/l.

The vegetative microorganism culture is added to the sterile broth containing the chloramphenicol.

The culture, which is kept stirring at a temperature of 21°–28° C., is aerated by blowing air at a rate of 0.5–1 volume/volume of broth/minute.

By way of example, a typical broth composition within the experimental range is as follows:

| | |
|---|---|
| Sodium glutamate | 3–8 g/l |
| KH$_2$PO$_4$ | 0.5–1.5 g/l |
| K$_2$HPO$_4$ | 3.1–8.4 g/l |
| Collagen hydrolyzate | 15–25 g/l |
| Corn steep liquor | 1–5 g/l |

-continued

| | |
|---|---|
| Glucose | 10–25 g/l |
| Yeast extract | 1–3 g/l |
| Chloramphenicol | 20–40 mg/l |

The fermentation time is 24–72 hours depending on the operating conditions, to obtain about 3000 U/l of Gl-7-ACA acylase.

3) Extraction and purification of the Gl-7-ACA acylase enzyme

Gl-7-ACA acylase is an endocellular enzyme. After fermentation the culture broth is centrifuged and the cells subjected to chemical treatment (addition of water-insoluble solvents and surfactants) or physical treatment (press or ball mill) for lysis of the cell membrane.

A preferred method is to resuspend the cell mass in an aqueous solution buffered at pH 8 by adding alkaline phosphates and then subject it to lysis in a Manton-Gaulin press at 500–600 bar. The cell lysate is flocculated by adding cationic polyelectrolytes and recentrifuged.

The clarified liquid containing the crude enzyme is purified by ultrafiltration, salting and extraction with solvents insoluble in the aqueous phase.

A preferred technique is to directly purify the clarified liquid after centrifuging, through a column containing ion exchange resin with the diethylaminoethyl group as the ionizable function (DEAE type).

A chromatographic resin which has proved very effective is Sepharose DEAE fast flow (Pharmacia). By eluting with scalar quantities of sodium chloride the Gl-7-ACA acylase can be obtained in a particularly pure form free of esterase.

Figure 4:
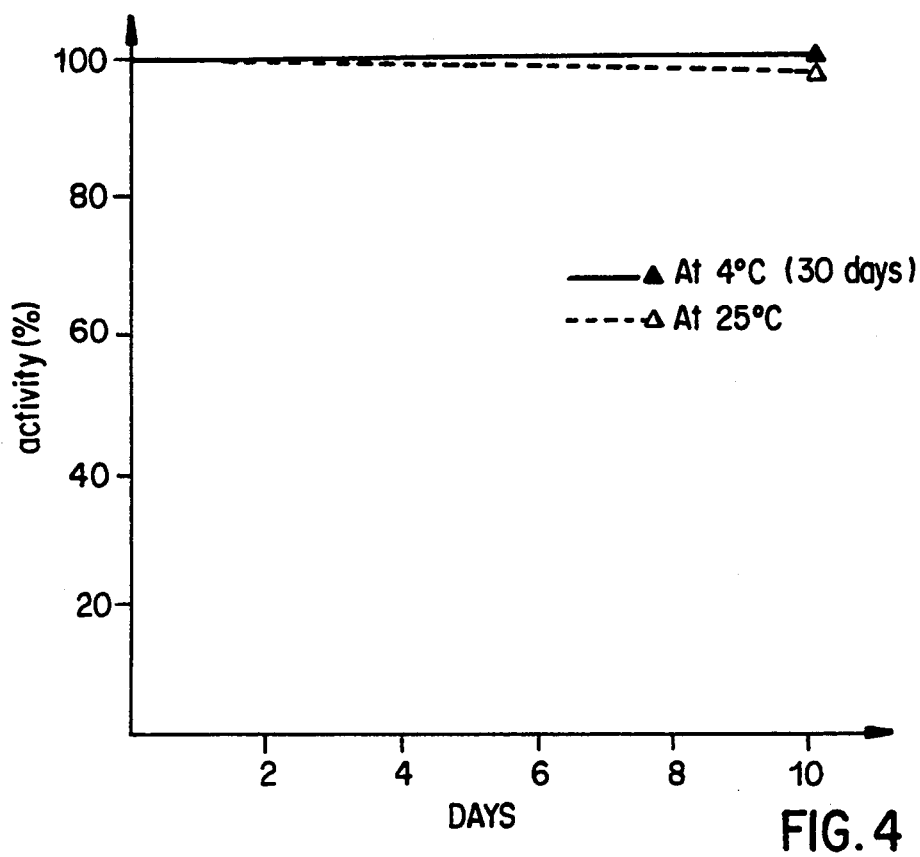
FIG. 4 is a graph of the stability of Gl-7-ACA acylase over time.

The purified Gl-7-ACA acylase obtained in this manner is very stable. It shows no loss of activity after 10 days at 25° C. or after 1 month at 4° C. (see FIG. 4).

4) Immobilization of the Gl-7-ACA acylase enzyme

The method consists of immobilizing this enzyme on solid supports such as artificial polymers and inorganic materials which are insoluble in the aqueous environment used in the enzymatic conversion of the glutaryl derivative (II) to 7-aminocephalosporanic acid (III).

Suitable resins for immobilizing the acylase are those of macroreticular strongly basic polystyrene structure type such as Amberlite 900 and Amberlite 904, or phenolformaldehyde resins with secondary or tertiary amino functional groups such as Duolite A 7 and Duolite A 568.

According to the present invention the enzyme is brought into contact with the resin, immobilized on it and stabilized by a bifunctional agent of the aliphatic dialdehyde type such as glutaraldehyde, by means of cross-linkage bonds between the enzymatic protein and the matrix.

Other resins suitable for immobilizing the acylase are those of polyacrylic structure crosslinked with divinylbenzene and functionalized with primary amino groups such as Duolite A 365.

Gl-7-ACA acylase has also been immobilized on acrylic resins with epoxide functional groups such as Eupergit C (Röhm Pharma) or on inorganic supports such as alumina, and in particular alumina impregnated with a polyethyleneimine/glutaraldehyde complex such as UOP IPS-200 (UOP-USA).

Table 2 shows the main characteristics of the matrices used and the corresponding immobilization data.

In the chosen range of 10–20 U of enzyme per g of wet support the attachment is practically complete, and the functionality of the immobilized enzyme is 70–80% expressed as percentage activity of the free enzyme.

Normally 20 U of Gl-7-ACA acylase are bound per gram of support to obtain the most favourable immobilization ratio and an activity after bonding sufficient to ensure good process operation in the transformation of the glutaryl derivatives into 7-aminocephalosporanic acids.

Figure 5:
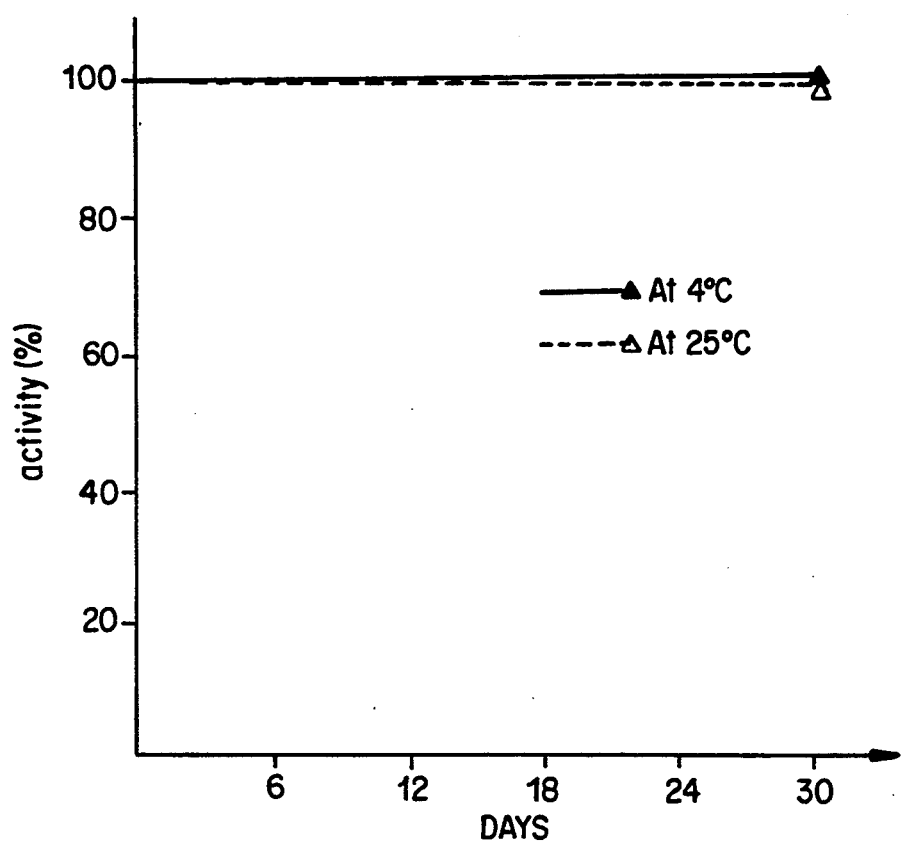
FIG. 5 is a graph of the stability of immobilized Gl-7-ACA acylase over time.
Figure 6:
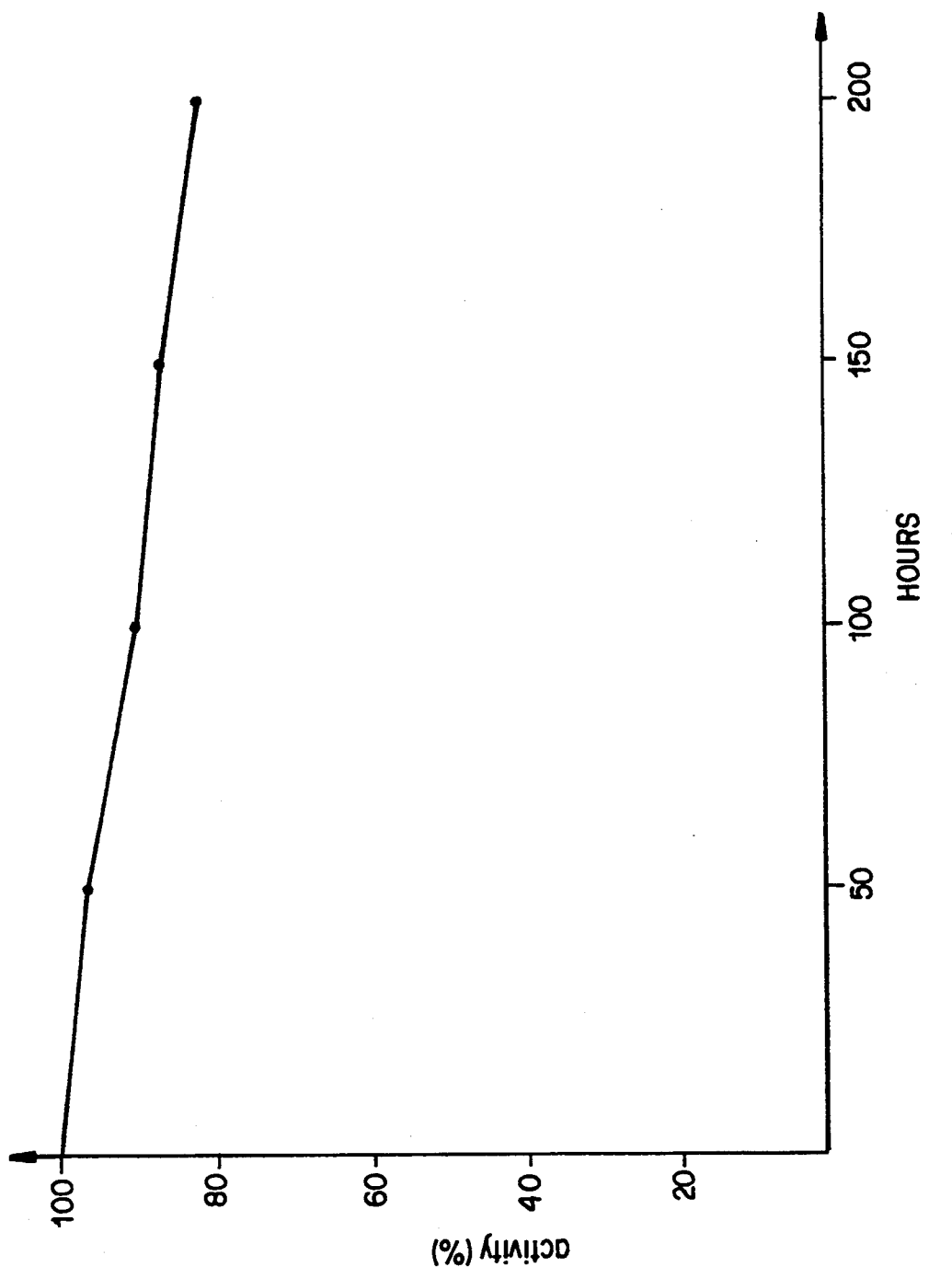
FIG. 6 is a graph showing the stability of immobilized Gl-7-ACA acylase during the process of converting glutaryl derivatives into 7-ACA or derivatives thereof.

As the graph of FIG. 5 shows, the immobilized Gl-7-ACA acylase is very stable at 4° and 25° C. It can be used for more than 200 process hours in the conversion of cephalosporanic compounds of type (II) (glutaryl derivatives) into those of type (III) (7-ACA or derivatives), as is clear from the graph of FIG. 6.

Measurement of Gl-7-ACA acylase activity

The activity of the Gl-7-ACA acylase enzyme is evaluated by measuring the rate of hydrolysis of the glutaryl-7-ACA to 7-ACA in 0.1 M pH 7.8 phosphate buffer at 37° C. The 7-ACA is determined spectrophotometrically against a standard curve, by measuring at 410 nm the yellow colour (Schiff's base) which forms with the reagent p-dimethylaminobenzaldehyde using the modified Bulasingham method (Biochem. Biophys. Acta 276, 250, 1972).

One unit of acylase is defined as that quantity of enzyme (in solution or immobilized) which under the conditions of the method produces one $\mu$ mole of 7-ACA in one minute.

The following examples and preparations are given to illustrate the implementation of both the first and second stages of the enzymatic process of the invention.

EXAMPLE 1

Production of D-amino acid oxidase by means of *Rhodotorula gracilis* ATCC 26217 culture A 100 l fermenter is charged with 70 l of broth having the following composition:

| | |
|---|---|
| NaCl | 0.5 g/l |
| $K_2HPO_4$ | 1.5 g/l |
| $MgSO_4.7H_2O$ | 1 g/l |
| $CaCl_2$ | 0.25 g/l |
| $ZnSO_4$ | 0.002 g/l |
| $FeCl_3$ | 0.003 g/l |
| Glucose | 25 g/l |
| D-alanine | 7 g/l |

The medium is adjusted to pH 5.6 with 2N $H_2SO_4$, sterilized at 120° C. for 20 minutes and cooled to 30° C. It is inoculated with a vegetative culture of *Rhodotorula gracilis* ATCC 26217 and fermented for 28 hours at 30° C. under stirring at 200 rpm and aeration at 0.5 l/l/min. During fermentation the pH is allowed to fall spontaneously to 5, at which it is maintained constant by automatic additions of 10% NaOH.

At the end of fermentation 72 l of culture broth are obtained with $OD_{660}=39$ and a D-amino acid oxidase activity of 4600 U/l. The broth is centrifuged at 5000 g in a Westfalia chamber centrifuge.

3.1 kg of cell paste are obtained (moisture about 80%) corresponding to 320,000 U of D-amino acid oxidase.

EXAMPLE 2

Extraction and purification of D-amino acid oxidase 1 kg of cell paste (103,000 U of DAO) obtained as described in Example 1 is dispersed in 3 litres of 25 mM pH 8 phosphate buffer containing 0.5 g/l of sodium metabisulphite and 0.5 g/l of cetylpyridinium chloride.

The suspension is cooled to 4° C. and passed through a Manton-Gaulin press at 550 bars.

The homogenized product (4.3 l) is flocculated by adding 20 ml of cationic polyelectrolyte (Nymco 2045C). The flocculate is clarified by filtering through Hyflo. The clarified product (4.9 l) is concentrated by ultrafiltration at 4° C. through a polysulphonic membrane of MW 30,000.

262 g of ammonium sulphate are added to the concentrate obtained by ultrafiltration (0.750 l).

The precipitate is separated from the supernatant by centrifuge and redissolved in 300 ml of 25 mM pH 8 phosphate buffer containing 0.5 g/l of sodium metabisulphite.

The solution (320 ml) is diafiltered by ultrafiltration through a membrane of MW 30,000.

The diafiltrate (340 ml) contains the crude DAO in a concentration of 224 U/ml.

The D-amino acid oxidase is purified by feeding the solution of crude enzyme through a Sepharose DEAE fast flow column (bed volume 800 ml, $\phi$ 5 cm, h 40 cm) and eluting with the same 25 mM pH 8 phosphate buffer. The DAO is not retained by the resin but is only slowed down in its travel, and passes into the percolate.

The interfering enzymes, in particular the esterase, are not eluted with the 25 mM pH 8 buffer and are displaced only during the regeneration of the column with 0.5M NaCl.

The purified D-amino acid oxidase is collected in a volume of 1230 ml with an activity of 52 U/ml and a specific activity of 19 U/mg proteins.

The total purification yield is 62%, corresponding to a total of 63920 U.

The purified D-amino acid oxidase is stable for at least 6 days at 4° C. and for at least 6 months at −20° C.

EXAMPLE 3

Immobilization of D-amino acid oxidase on Duolite A 365

35 g of Duolite A 365 resin with a particle size of 100–200 $\mu$m are treated with 0.5 l of 100 mM pH 8 potassium phosphate buffer. After 15 minutes of stirring the pH is adjusted by sequential additions of 10% $H_3PO_4$ (6 ml). When the pH is constant at 8 the supernatant is removed by filtration. 400 ml of 2% glutaraldehyde in 25 mM pH 8 potassium phosphate buffer are added to the wet resin. It is left stirring for 30 minutes at a temperature of 20°–25° C., after which the supernatant is separated by filtration to obtain a wet solid mass.

386 ml of a D-amino acid oxidase solution (52 U/ml; 19 U/mg proteins) purified as in Example 2 are added to the wet activated resin mass. The system is kept under mild stirring for 12 hours at 4° C. The immobilization yield, calculated on the concentration of the spent supernatant, is 100%.

The product is filtered and the wet mass washed with 0.5M NaCl in 25 mM pH 8 potassium phosphate buffer and then with 25 mM pH 7.5 potassium phosphate buffer.

103 g of immobilized D-amino acid oxidase are obtained with an activity of 48 U/g of wet product.

EXAMPLE 4

Immobilization of D-amino acid oxidase on Eupergit C 4.5 g of Eupergit C (150 μm) are added under stirring to 120 ml of 1M pH 8 potassium phosphate buffer cooled to 4° C., followed by 55 ml of a D-amino acid oxidase solution (58 U/ml; 17 U/mg proteins) obtained as in Example 2. The system is left under mild stirring for 2 hours at 4° C. and the product recovered by filtration. 15.7 g of wet D-amino acid oxidase immobilized on Eupergit C are finally obtained with an activity of 58 U/g of wet product.

EXAMPLE 5

Immobilization of D-amino acid oxidase on UOP IPS-200

80 ml of a D-amino acid oxidase solution (45 U/ml; 17 U/mg proteins) purified as in Example 2 are diluted with 80 ml of 1M pH 7.5 potassium phosphate buffer.

The solution at 4° C. is recycled at 600 ml/hour through a column ($\phi$ 2 cm; h 8 cm) containing 20 g of UOP IPS-200 for 4 hours. After this time 91% of the D-amino acid oxidase activity is immobilized. 19 g of a filtered wet mass are obtained with an activity of 21 U/g.

EXAMPLE 6

Transformation of Cephalosporin C to glutaryl-7-ACA by means of D-amino acid oxidase immobilized on Duolite A 365

A) Batch conversion 66 g of Cephalosporin C sodium salt dihydrate (purity 90.9%) are dissolved in 2 l of pH 8 potassium phosphate buffer at a concentration of 25 mM containing 0.5 g of sodium metabisulphite.

The Cephalosporin C solution is fed into a 3 litre reactor with 150 g of wet D-amino acid oxidase immobilized on Duolite A 365 as in Example 3.

Incubation is conducted at 25° C. under slight stirring and with an oxygen flow through a bottom diffuser of 1 vol/vol/min.

The pH is maintained at 7.5 by automatic additions of 5% ammonia.

In 75 minutes the Cephalosporin C is completely transformed. The percentage composition of the cephalosporinic transformation products is:

| Glutaryl-7-ACA | 90.1% |
|---|---|
| Ketoadipyl-7-ACA | 6.2% |
| Glutaryl-7-ACA desacetyl | 1.1% |
| Glutaryl-7-ACA desacetoxy | 0.9% |
| Glutaryl-7-ACA sulphoxide | 0.8% |
| Other β-lactams | 0.9% |

To transform the residual ketoadipyl-7-ACA to glutaryl-7-ACA, the solution obtained after incubation is separated from the immobilized enzyme mass by filtration. 10 ml of 3.5% hydrogen peroxide are added under stirring, for each litre of filtrate. The mixture is left for 15 minutes at 25° C. after which 0.5 g of sodium pyruvate are added.

The percentage composition on termination of treatment is:

| Glutaryl-7-ACA | 95.5% |
|---|---|
| Ketoadipyl-7-ACA | 0.1% |
| Glutaryl-7-ACA desacetyl | 1.1% |
| Glutaryl-7-ACA desacetoxy | 0.9% |
| Glutaryl-7-ACA sulphoxide | 1.5% |
| Other β-lactams | 0.9% |

The enzymatic load was tested for 100 cycles over periods of 75–120 minutes.

Total production was 4760 g of glutaryl-7-ACA equivalent to 31.7 g of glutaryl-7-ACA per g of immobilized enzyme.

B) Continuous column conversion

A 15 g/l solution of Cephalosporin C in the form of the sodium salt dihydrate in 0.1M pH 8 phosphate buffer was passed at a rate of 1 litre/hour through five columns ($\phi$ 40 mm) each containing 100 g (150 ml apparent volume) of DAO immobilized on Duolite A 365 (see Example 3).

The entire system, which operates continuously with the columns connected in series, is temperature-controlled at 25° C. and maintained at 3 bar with oxygen injection after each column.

At the exit of the fifth column the Cephalosporin C residue is about 1%, the conversion to glutaryl-7-ACA being 92% of the stoichiometric (11.2 g/l).

EXAMPLE 7

Transformation of Cephalosporin C to glutaryl-7-ACA by means of D-amino acid oxidase immobilized on Eupergit C 2 l of the Cephalosporin C solution prepared as in Example 6 are incubated with 150 g of D-amino acid oxidase immobilized on Eupergit C (as in Example 4). The incubation is conducted at 25° C. in an oxygen stream.

After 60 minutes at pH 7.5 the Cephalosporin C is completely transformed, with a glutaryl-7-ACA yield of 91% and a ketoadipyl-7-ACA yield of 5.8%.

The solution is separated from the immobilized enzyme by filtration.

1 litre of filtrate is treated with 10 ml of 3.5% hydrogen peroxide and after 15 minutes with 0.25 g of sodium metabisulphite.

The final composition of the transformation product is:

| Glutaryl-7-ACA | 96.1% |
|---|---|
| Glutaryl-7-ACA desacetyl | 0.9% |
| Glutaryl-7-ACA desacetoxy | 0.7% |
| Glutaryl-7-ACA sulphoxide | 0.8% |
| Other β-lactams | 1.5% |

The enzymatic load was tested for 100 cycles. Total production was 4700 g of glutaryl-7-ACA equivalent to 31 g/g of immobilized enzyme.

EXAMPLE 8

Transformation of Cephalosporin C to glutaryl-7-ACA by means of D-amino acid oxidase immobilized on UOP IPS-200

6.57 g of Cephalosporin C sodium salt dihydrate (purity 91.3%) are dissolved in 200 ml of water. 0.68 g of $KH_2PO_4$ and 0.1 g of sodium metabisulphite are added to the solution and the pH corrected to 7.5 with 5% NaOH.

This cephalosporin solution is pumped through a column temperature-controlled at 25° C. and containing 20 g of D-amino acid oxidase immobilized on UOP IPS-200 ($\phi$ 3 cm; h 4 cm; bed volume 28 ml). The flow rate is maintained at 50 ml/min. The solution leaving the column is collected in a vessel and oxygenated via an oxygen diffuser, corrected to pH 7.5 and recycled for two hours.

After two hours of recycling the Cephalosporin C conversion is complete.

The solution (100 ml) is treated with 1 ml of 3.5% $H_2O_2$ and after 15 minutes with 50 mg of sodium pyruvate.

The percentage composition of the transformation product is:

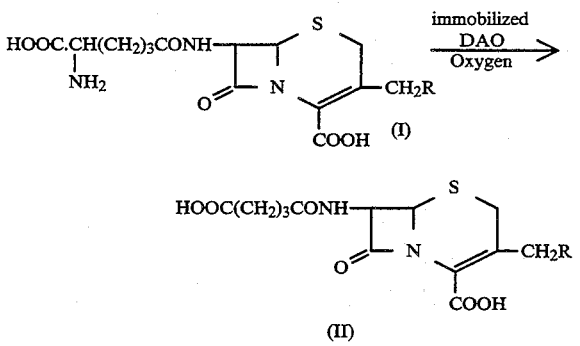

Second stage:

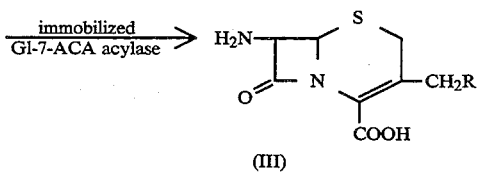

The experiment was conducted for 60 cycles with a total glutaryl-7-ACA production of 280 g, equivalent to 14 g/g of immobilized enzyme.

EXAMPLE 9

Production of Gl-7-ACA acylase by means of an E. coli ATCC 9637 (pJc 200) culture 1) Preparation of the microorganism E. coli ATCC 9637 (pJc 200)

a) Preparation of the plasmid pACYC 184.

The strain E. coli ATCC 37033 containing the plasmid vector pACYC 184 (Tet$^r$, Cam$^r$) is incubated for 16 hours at 37° C. in 0.5 l of LB culture medium containing 10 g/l of Bacto Tryptone Difco, 5 g/l of Bacto Feast extract Difco and 10 g/l of NaCl.

The cells obtained are sedimented, washed, lysed and the plasmid isolated by the alkaline method (T. Maniatis et al., Molecular Cloning: A Laboratory Manual, Cold Spring Harbor Laboratory, 1982). The plasmid DNA obtained is then purified by centrifuging in a CsCl gradient.

b) Preparation of the DNA donor containing the genetic information relative to glutaryl-7-ACA acylase production.

The strain of the Acinetobacter ATCC 53891 species which produces Gl-7-ACA acylase is cultivated in a medium containing 5 g/l acid sodium glutamate, 1.5 g/l $KH_2PO_4$, 5 g/l NaCl, 25 g/l collagen hydrolyzate, 5 g/l corn steep liquor and 2 g/l glucose. The system is incubated for 48 hours at a temperature of 25° C.

The cells obtained are then sedimented, washed and lysed with SDS 1%, ETDA 20 mM and proteinase-K 0.1 mg/ml.

The lysed mixture is heated to 55° C. for 3 hours, then extracted a number of times with phenol and chloroform-isoamyl alcohol. The DNA is precipitated in the aqueous phase by ethanol.

The precipitated DNA is washed with 100% ethanol and 70% ethanol, and dissolved in a 10 mM pH 7.5 Tris-HCl buffer containing 1 mM ETDA.

c) Insertion of the DNA donor fragments into the vector.

Various samples containing 1 $\mu$g of the DNA obtained from the Acinetobacter sp. ATCC 53891 strain are digested with the BamHI restriction endonuclease at 37° C. and the reaction blocked at different times by heating the sample to 65° C. for 10 minutes. In this manner different partial DNA digestions are obtained, these being displayed by coloration with ethidium bromide after electrophoresis on agarose gel.

Various samples containing 2 $\mu$g of plasmid pACYC 184 DNA are digested with the BamHI restriction endonuclease at 37° C. for 1 hour, then heating to 65° C. for 10 minutes to block the reaction. Each sample of the partial BamHI digestions of the Acinetobacter DNA is bound to a sample of the BamHI digestion of the pACYC 184 plasmid by T4 DNA ligase in the presence of ATP, $Mg^{2+}$ ions and 2-mercaptoethanol for 16 hours at 14° C.

Various collections of recombinant vectors containing DNA fragments of the Acinetobacter ATCC 53891 species inserted into the plasmid pACYC 184 are obtained by this procedure.

d) Selection of the carrier plasmid for the coding gene for the Gl-7-ACA acylase enzymatic activity.

E. coli HB101 is transformed by the gene library of the Gl-7-ACA acylase producer strain of the species Acinetobacter, selecting the Gl-7-ACA acylase gene carrier transformers for their capacity to grow at 37° C. in the basic medium M9 to which 0.2 g/dl glucose, 0.1 mg/dl thiamine-HCl, 10 mg/dl proline, 5 mg/dl glutaryl-leucine and 5 mg/dl chloramphenicol have been added (T. Maniatis et al., Molecular Cloning: A Laboratory Manual, Cold Spring Harbor Laboratory, 1982). In this manner the strain E. coli HB101 (pJC11) is obtained.

The plasmid pJC11 is characterised by possessing the chloramphenicol resistance gene and the Gl-7-ACA acylase gene (localized in a DNA fragment of about 8.5 kb partially digested with BamHI) expressed under the control of the gene promoter for tetracycline resistance [Bolivar et al., (1977) Gene 2:95).

Figure 7:
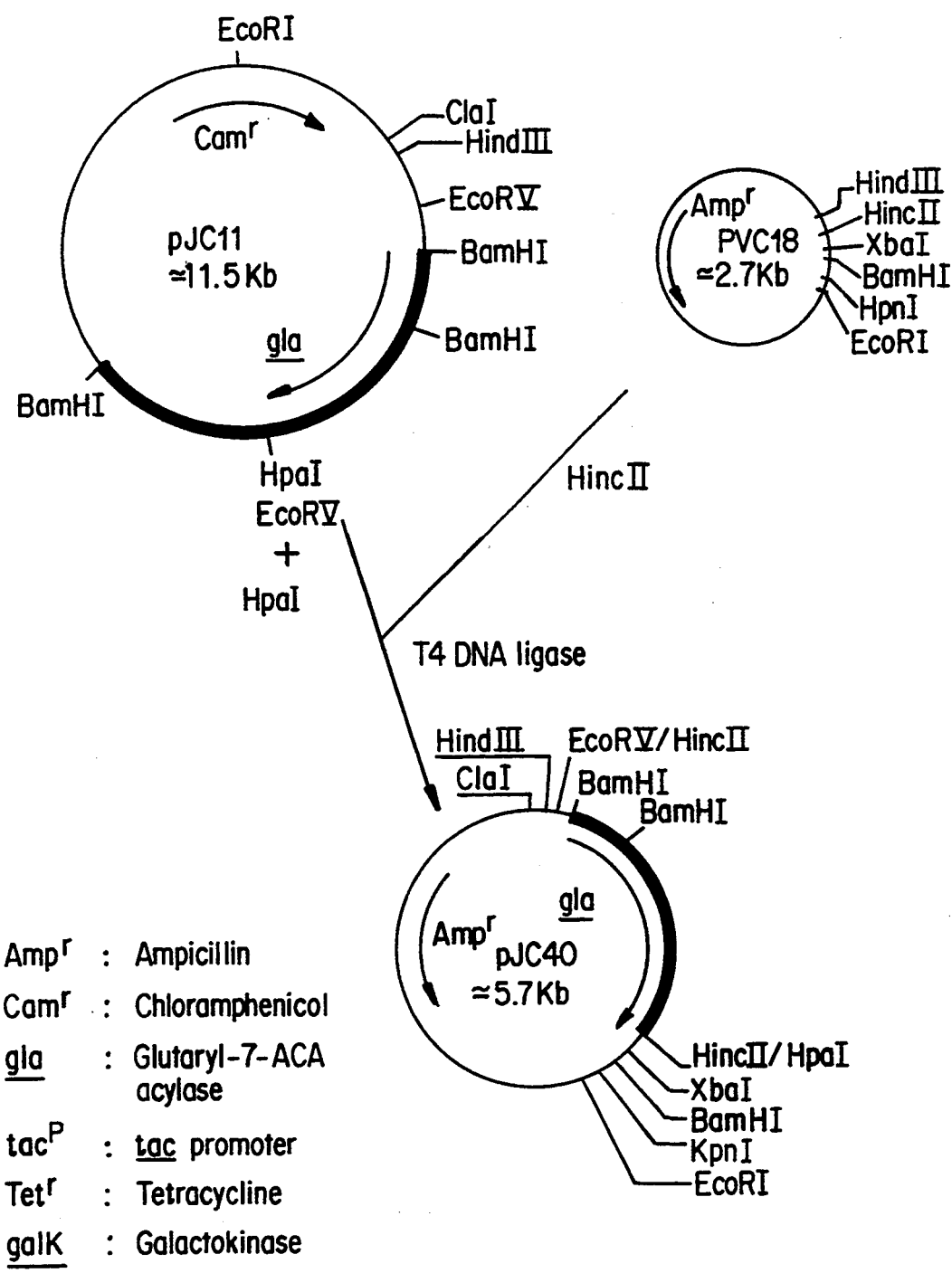
FIG. 7 shows the production of the plasmid pJC40.

After digesting 5 $\mu$g of pJC11 DNA with EcoRV and HpaI endonuclease and purifying a 3 kb Gl-7-ACA acylase gene carrier fragment, this is bound to the plasmid pUC18 previously digested with HimcII and dephosphorylated. The resultant plasmid is named pJC40 (see FIG. 7).

5 $\mu$g of the plasmid pDR540 [de Boer et al., (1983) Proc. Natl. Acad. Sci. USA 80:21] are digested with BamHI endonuclease and are then dephosphorylated under the conditions described by T. Maniatis et al., Molecular Cloning: A Laboratory Manual, Cold Spring Harbor Laboratory, 1982.

Starting from pJC40 a 3 kb partial BamHI Gl-7-ACA acylase gene carrier fragment is purified and bound to the BamHI site of the plasmid pDR540.

Figure 8:
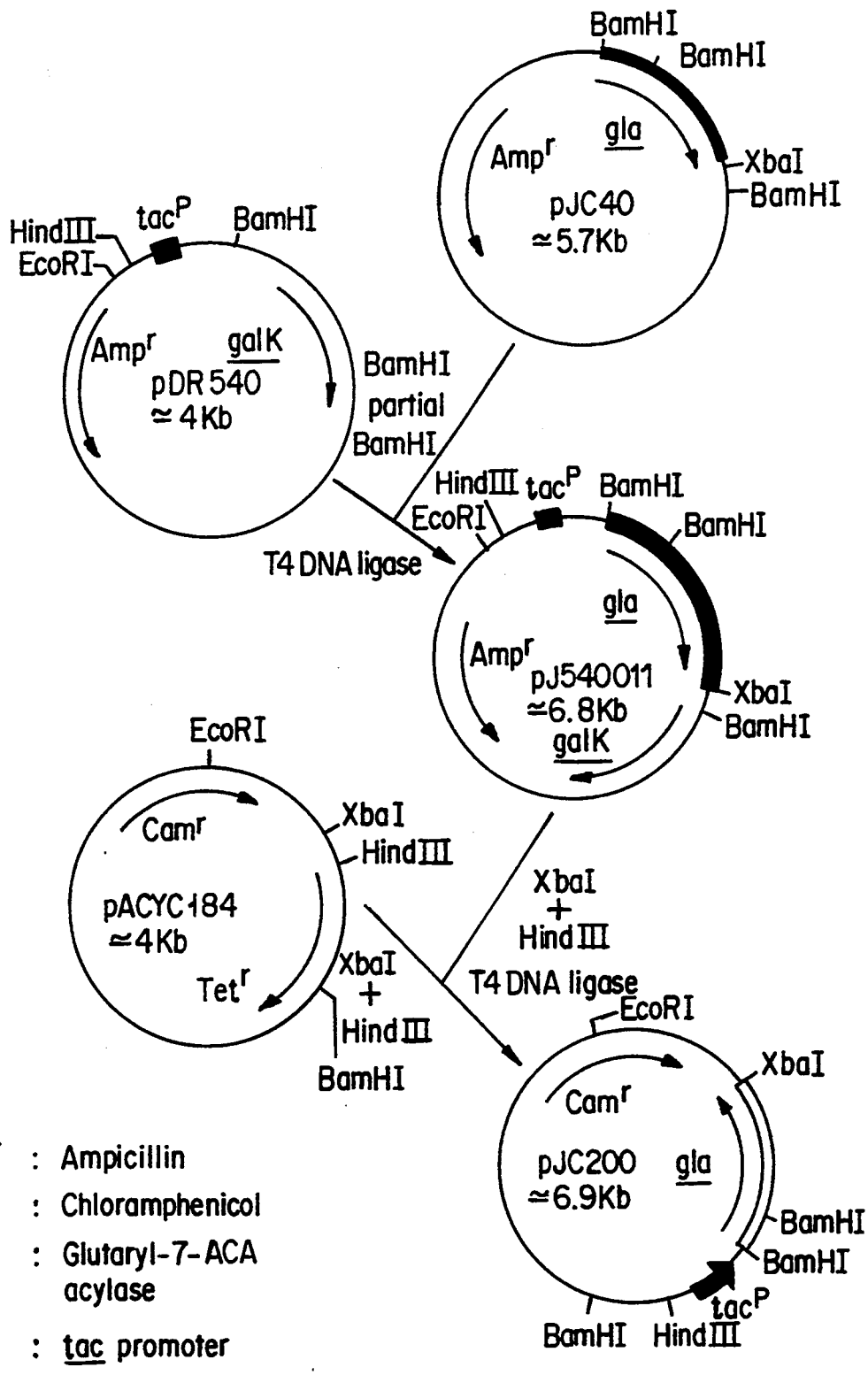
FIG. 8 shows the production of the plasmid pJC200.

The resultant vector is named pJC54011 (see FIG. 8).

e) Construction of the plasmid pJC 200.

5 μg of the plasmid pACYC-184 are digested with XbaI and HindIII restriction endonuclease under the conditions described in Biochemicals Catalogue, Boehringer Mannheim GmbH (1987) and are then bound to a fragment of DNA XbaI-HindIII Gl-7-ACA acylase gene carrier deriving from pJC54011. The resultant plasmid is named pJC 200 (see FIG. 8). All the techniques used in handling these DNAs are described by T. Maniatis et al., Molecular Cloning: A Laboratory Manual, Cold Spring Harbor Laboratory, 1982.

The plasmid pJC 200 is characterised by possessing the chloramphenicol resistance gene as selection marker in $E.$ $coli$ and the coding gene for Gl-7-ACA acylase activity of the species Acinetobacter ATCC 53891 expressed under the control of the tac promoter.

f) Transformation of $E.$ $coli$ ATCC 9637 with the high expression vector pJC 200.

The introduction of the plasmid pJC 200 into non-β-lactamase producing $E.$ $coli$ ATCC 9637 is achieved by the method described by Hanahan, J. Mol. Biol., 166, 557–580 (1983).

The $E.$ $coli$ ATCC 9637 cells are firstly grown in SOB medium at 37° C. and 250 rpm until $OD_{600}$=0.45. The culture is then centrifuged at 3000 g at 4° C. for 10 minutes and the cells resuspended in ⅓ of the initial volume of RF1. After incubation in ice for 15 minutes and centrifuging under the same conditions the cells are resuspended in 1/12.5 of the initial volume of RF2. The mixture is again incubated in ice for 15 minutes.

The cells thus obtained, known as "competent", are characterised by their capacity to accept exogenous DNA with great efficiency.

This DNA is introduced by mixing 10 ng of the plasmid pJC 200 with 100 μl of competent cells, the mixture then being incubated in ice for 30 minutes.

After thermal shock at 42° C. for 60 seconds, 800 μl of SOB medium are added and the system incubated at 37° C. and 200 rpm for 60 minutes.

Selection of transformers is concluded in the LB medium with 30 μg/ml of chloramphenicol added.

The microorganism obtained, which has high Gl-7-ACA acylase productive capacity, is named $E.$ $coli$ ATCC 9637 (pJC 200).

The LB, SOB, RF1 and RF2 compositions are described by Maniatis et al., Molecular Cloning: A Laboratory Manual, Cold Spring Harbor Laboratory, 1982.

2) Fermentation a) Vegetative phase $E.$ $coli$ ATCC 9637 (pJC 200) cells are grown at 28° C. for 24 hours on a 180×10 mm slant with solid medium comprising tryptone (10 g/l), yeast extract (5 g/l), NaCl (5 g/l), chloramphenicol (30 mg/l) and agar (15 g/l) at pH 7.5 and are taken up in 5 ml of sterile physiological solution.

0.5 ml of this cell suspension are transferred to 500 ml flasks containing 100 ml of vegetative medium of the following composition: tryptone (12 g/l), yeast extract (24 g/l), glucose (5 g/l), $KH_2PO_4$ (1.1 g/l), $K_2HPO_4$ (6.2 g/l) and chloramphenicol (30 mg/l).

The culture is grown at 28° C. and 250 rpm for 24 hours until $OD_{600}$=15–18.

b) Productive phase

A 100 l fermenter containing 58 l of broth of the following composition: acid sodium glutamate (6 g/l), yeast extract (3 g/l), collagen hydrolyzate (20 g/l), corn steep liquor (3 g/l), $KH_2PO_4$ (1.1 g/l) and $K_2HPO_4$ (6.2 g/l) is sterilized at 120° C. for 20 minutes and cooled to 23° C., after which separately sterilized glucose (6 g/l) and chloramphenicol (30 mg/l) are added.

The medium is inoculated with 2% of the vegetative culture obtained as in the preceding point. The fermentation is conducted for 72 hours at 23° C. with aeration of 0.5 v/v/min aeration, stirring at 200 rpm, and the addition of 3 g/l of glucose every 12 hours.

At the end of fermentation 63 l of culture broth are obtained having a pH of 8, an $OD_{600}$ of 28 and a Gl-7-ACA acylase activity of 2790 U/l.

On centrifuging at 6000 g 1.8 kg of cell paste (moisture 80%) are recovered corresponding to a total of 166980 U of Gl-7-ACA acylase.

EXAMPLE 10

Extraction and purification of Gl-7-ACA acylase 1 kg of cell paste (92766 U of Gl-7-ACA acylase) obtained as described in Example 9 are dispersed in 2 litres of 25 mM pH 8 potassium phosphate buffer. The suspension is cooled to 4° C. and passed twice through a Manton-Gaulin press at 550 bar. The lysate is made up to 6 litres with 25 mM pH 8 potassium phosphate buffer and flocculated by adding 6 ml of Nymco 2045 C cationic polyelectrolyte. The flocculate is clarified by centrifuging at 6000 g.

5.5 l of clarified product are obtained with a Gl-7-ACA acylase activity of 13915 U/l, equivalent to a total of 76532 U.

The clarified product is concentrated by ultrafiltration through a polysulphonic membrane of MW 50000.

The crude concentrate of 1580 ml (Gl-7-ACA acylase=48 U/ml; protein=45 mg/ml) is fed through a column containing 1 litre of Sepharose DEAE balanced with 25 mM pH 8 potassium phosphate buffer. The Gl-7-ACA acylase is eluted in a volume of 2170 ml with the same buffer to which 0.15 M of NaCl has been added.

The purified enzyme has an activity of 20.3 U/ml and a specific activity of 2.6 U/mg proteins.

EXAMPLE 10 bis

Preparation of Gl-7-ACA acylase by means of cultures of Escherichia coli P-3 (pJC200) registration No. NCIMB 40433

$E.$ $coli$ P-3 having registration number NCIMB 40432 (non-β-lactamase producing microorganism) has been cloned with the gene of Gl-7-ACA acylase isolated from the Acinetobacter species having registration number ATCC 53891. The $E.$ $coli$ P-3 (pJC200) registration No. NCIMB 40433 thus obtained is fermented in medium TB (see Maniatis et al. mentioned in example 9) during 48 hours at 21° C. After sedimentation of the cells the enzyme Gl-7-ACA acylase is separated from cell paste through sonication.

The activity of the Gl-7-ACA acylase thus obtained results to be 2U/mg proteins.

EXAMPLE 11

Immobilization of Gl-7-ACA acylase on Duolite A 568

40 g of Duolite A 568 resin with a particle size of 100–300 μm are treated with 0.6 l of 100 mM pH 8 potassium phosphate buffer. After 15 minutes of stirring the pH is adjusted by sequential additions of 10% $H_3PO_4$ (12 ml). When the pH is constant at 8 the supernatant is removed by filtration. 500 ml of 2% glutaraldehyde are added to the wet resin. The system is left stirring for 15 minutes at ambient temperature, after which the liquid is separated by filtration to obtain a wet solid mass.

200 ml of Gl-7-ACA acylase solution (10.8 U/ml; 2.4 U/mg proteins) purified as in Example 10 are added to the wet activated mass. The system is kept under mild stirring for 12 hours at 4° C. 5 ml of 25% glutaraldehyde are then added and stirring continued for more than 6 hours at 4° C.

The product is then filtered and the wet mass washed with 500 ml of 0.5M NaCl in 25 mM pH 8 potassium phosphate buffer, and then with the same buffer but without the sodium chloride.

108 g (wet mass) of immobilized Gl-7-ACA acylase are obtained with an activity of 19 U/g and an attachment yield of 100%.

The immobilized enzyme is stored under 25 mM pH 8 potassium phosphate buffer and is stable for at least one month at 25° C. and 6 months at 4° C.

EXAMPLE 12

Immobilization of Gl-7-ACA acylase on Eupergit C 10 g of Eupergit C (150 μm) are added to 250 ml of 1M pH 8 potassium phosphate buffer at 20° C., followed by 120 ml of a Gl-7-ACA acylase solution (10.8 U/ml; 2.4 U/mg proteins) obtained as in Example 10. The system is left under mild stirring for 6 hours at 20° C. and the resin recovered by filtration. The wet mass is washed with 25 mM pH 8 potassium phosphate buffer. 34 g of wet immobilized Gl-7-ACA acylase are finally obtained with an activity of 31 U/g, equivalent to 81% of the enzymatic activity for immobilization.

EXAMPLE 13

Immobilization of Gl-7-ACA acylase on UOP IPS-200

25 ml of Gl-7-ACA acylase solution (16.4 U/ml; 2.2 U/mg proteins) purified as in Example 10 are diluted with 75 ml of 1M pH 7.5 potassium phosphate buffer. The enzyme solution at 4° C. is recycled at 1 l/hour through a column (φ 2 cm; h 8 cm) containing 20 g of UOP IPS-200.

After 4 hours of recycling the column is washed with 25 mM pH 8 potassium phosphate buffer.

The wet immobilized enzyme mass (22 g) has an activity of 14 U/g, equivalent to 75% of the initial enzyme fed to the reaction.

EXAMPLE 14

Transformation of glutaryl-7-ACA with Gl-7-ACA acylase immobilized on Duolite A 568

500 g of Gl-7-ACA acylase immobilized on Duolite A 568 (Example 11) are loaded into five columns (φ 22 mm). The enzymatic load is distributed in the following proportions: 1st column 50 g; 2nd column 75 g; 3rd column 100 g; 4th column 125 g; 5th column 150 g. A glutaryl-7-ACA solution (22.8 g/l; pH 8; 25° C.) obtained by enzymatic transformation of Cephalosporin C with immobilized D-amino acid oxidase is pumped through the first column of the series at a rate of 2 l/h. The percolate from the first column is recorrected in line to pH 8 and pumped through the second.

The operation is repeated for all columns of the series to obtain continuous flow conversion. At its exit from the fifth column the solution has the following composition:

| | |
|---|---|
| 7-ACA | 85.80% |
| Glutaryl-7-ACA | 9.04% |
| 7-ACA desacetyl | 1.70% |
| 7-ACA desacetoxy | 0.80% |
| 7-ACA sulphoxide | 1.70% |
| Cephalosporin C | 0.12% |
| Ketoadipyl-7-ACA | 0.14% |

The 7-ACA production after 200 hours is 5480 g. The total transformation yield is 83.5%.

The 7-ACA crystal is recovered as follows: 10 l of solution leaving the fifth column are adjusted to pH 6 with 2M HCl and concentrated by osmosis at 4° C. to a volume of 4.5 l, The pH of the concentrate is adjusted to 3.5 and the crystal recovered by filtration.

Crystallization yield: 94.5%. Purity of 7-ACA crystal: 97%.

EXAMPLE 15

Transformation of glutaryl-7-ACA to 7-ACA with Gl-7-ACA acylase immobilized on Eupergit C 12 g of Gl-7-ACA acylase immobilized on Eupergit in accordance with Example 12 are added to 150 ml of glutaryl-7-ACA solution (20.3 g/l) obtained by enzymatic transformation of Cephalosporin C with immobilized D-amino acid oxidase.

The system is incubated under stirring at 25° C. maintaining the pH at 8 by automatic addition of 5% ammonia.

Maximum transformation is obtained after 50 minutes with a 7-ACA conversion yield of 86%.

EXAMPLE 16

Transformation of glutaryl-7-ACA to 7-ACA with Gl-7-ACA acylase immobilized on UOP 200 IPS-200

50 g (wet weight) of enzyme acylase immobilized on UOP IPS-200 as in Example 13 are loaded into a column (φ 4 cm; h 5 cm).

500 ml of a 1% glutaryl-7-ACA solution are recycled through the column at a rate of 50 ml/min.

The pH is maintained constant at 7.8 by automatic addition of 5% ammonia. After 60 minutes 93% of the glutaryl-7-ACA has been transformed into 7-ACA.

The solution, separated from the enzymatic mass, is adjusted to pH 3.5 by adding 2N HCl and left overnight at 4° C. 3.7 g of 7-ACA are recovered. Purity 98%.

TABLE 1

| | | | | Immobilization of DAO produced from *Rhodotorula gracilis* | | | |
|---|---|---|---|---|---|---|---|
| Support (comm. name) | Area $m^2/g$ | Pores ∅ nm | Active function | $U/g^{(a)}$ immob. | $\%^{(b)}$ immob. enzyme | $U/g^{(c)}$ wet support | Functionality$^{(d)}$ % |
| Duolite A 365 | 50–60 | 40–50 | Primary amine | 100 | 100 | 31 | 31 |
| | | | | 200 | 100 | 46 | 23 |
| | | | | 400 | 80 | 52 | 13 |
| Duolite | 60–70 | 15–25 | Secondary | 100 | 100 | 29 | 29 |

TABLE 1-continued

Immobilization of DAO produced from *Rhodotorula gracilis*

| Support (comm. name) | Area m²/g | Pores ∅ nm | Active function | U/g[a] immob. | %[b] immob. enzyme | U/g[c] wet support | Functionality[d] % |
|---|---|---|---|---|---|---|---|
| A 7 | | | amine | 200 | 100 | 41 | 20.5 |
| | | | | 400 | 90 | 50 | 12.5 |
| Duolite A 568 | 55–65 | 15–30 | Tertiary amine | 200 | 100 | 45 | 22.5 |
| | | | | 400 | 100 | 52 | 13 |
| | | | | 600 | 93 | 61 | 10.1 |
| Amberlite IRA 900 | 25–30 | 30–40 | Quaternary amine | 100 | 100 | 18 | 18 |
| | | | | 200 | 99 | 33 | 16.5 |
| | | | | 400 | 70 | 40 | 10 |
| Eupergit C | 160–180 | 30–40 | Epoxide | 200 | 100 | 56 | 28 |
| | | | | 400 | 100 | 63 | 15.7 |
| | | | | 600 | 95 | 75 | 12.5 |
| UOP IPS 200 | 150–160 | 70–80 | Polyamine-glutaraldehyde | 100 | 100 | 17 | 17 |
| | | | | 200 | 95 | 21 | 10.5 |
| | | | | 400 | 70 | 28 | 7 |

[a]units of free enzyme reacted with 1 g of wet support
[b]quantity of immobilized enzyme expressed as percentage of free enzyme reacted
[c]activity of immobilized enzyme, in U/g of wet support
[d]activity of immobilized enzyme, expressed as percentage of the corresponding activity of the free enzyme reacted

TABLE 2

Immobilization of Gl-7-ACA acylase produced from *E. coli* ATCC 9637 (pJC200)

| Support (comm. name) | Area m²/g | Pores ∅ nm | Active function | U/g[a] immob. | %[b] immob. enzyme | U/g[c] wet support | Functionality[d] % |
|---|---|---|---|---|---|---|---|
| Duolite A 365 | 50–60 | 40–50 | Primary amine | 5 | 100 | 5 | 100 |
| | | | | 10 | 100 | 10 | 100 |
| | | | | 20 | 60 | 12 | 60 |
| Duolite A 7 | 60–70 | 15–25 | Secondary amine | 5 | 100 | 4.5 | 90 |
| | | | | 10 | 100 | 8.9 | 89 |
| | | | | 20 | 88 | 15 | 75 |
| Duolite A 568 | 55–65 | 15–30 | Tertiary amine | 20 | 100 | 19 | 95 |
| | | | | 30 | 100 | 25 | 83 |
| | | | | 50 | 90 | 35 | 70 |
| Amberlite IRA 900 | 25–30 | 30–40 | Quaternary amine | 10 | 100 | 9 | 90 |
| | | | | 20 | 100 | 17 | 85 |
| | | | | 30 | 90 | 25 | 83 |
| Eupergit C | 160–180 | 30–40 | Epoxide | 20 | 100 | 16 | 80 |
| | | | | 40 | 100 | 30 | 75 |
| | | | | 60 | 94 | 41 | 68 |
| UOP IPS 200 | 150–160 | 70–80 | Polyamine-glutaraldehyde | 10 | 100 | 9.6 | 96 |
| | | | | 20 | 95 | 14 | 70 |
| | | | | 30 | 81 | 21 | 70 |

[a]units of free enzyme reacted with 1 g of wet support
[b]quantity of immobilized enzyme expressed as percentage of free enzyme reacted
[c]activity of immobilized enzyme, in U/g of wet support
[d]activity of immobilized enzyme expressed as percentage of the corresponding activity of the free enzyme reacted

We claim:

1. In an enzymatic process for producing 7-amino cephalosporanic acid or its derivatives from Cephalosporin C or its derivatives in accordance with the following reaction scheme:

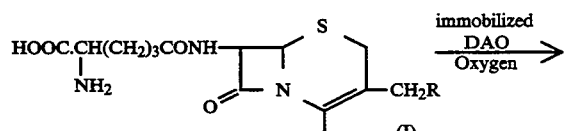

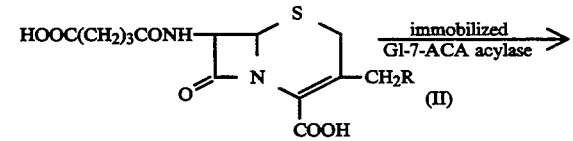

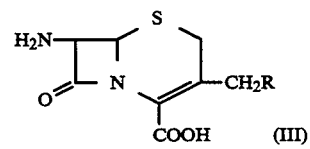

where R is —OCOCH₃, —H, —OH, —OCONH₂, by means of the enzyme D-amino acid oxidase (DAO) and subsequent transformation of the glutaryl derivatives (II) into 7-amino cephalosporanic acid (III) by means of the enzyme glutaryl-7-amino cephalosporanic acid acylase (Gl-7-ACA acylase), the improvement consisting of:

1a) preparing an enzyme DAO, free frown interfering enzymes selected from the group consisting of catalase, esterase and β-lactamase, from a *Rhodotorula gracilis* ATCC 26217 at 26°–30° C. and pH 4.8–5.5, by a process comprising the cells and obtaining a cell paste, subjecting the cell paste to lysis, separating the enzyme from the cell debris and purifying the enzyme by chromatography over an ion exchange resin with diethylaminoethyl groups as ionizable functions (DEAE resin);

1b) immobilizing the purified enzyme on an inert solid support which is insoluble in an aqueous medium and contains functional groups suitable for forming cross-linkages with the enzymatic protein, such support being selected from the group consisting of: strongly basic resins of macroreticular polystyrene structure with a quaternary amine function; weakly basic resins of macroreticular polystyrene structure with a primary amino function; porous alumina impregnated with a complex of polyethylenimine and glutaraldehyde; phenolformaldehyde resins with secondary or tertiary amino functional groups; and polyacrylic resins with terminal epoxide functional groups;

1c) carrying out the oxidative deamination of the Cephalosporin C or its derivatives (I) by bringing the immobilized enzyme obtained in 1b) into contact with an aqueous solution of said compound at a concentration of 20–60 g/l, at pH 7–8, and at a temperature of 20°–30° C. in the presence of oxygen or air;

1d) separating the supported enzyme from the aqueous reaction mixture and adding hydrogen peroxide in an amount equal to or in excess of the stoichiometric quantity required to convert the residual ketoadipylcephalosporanic acid into glutaryl-7-aminocephalosporanic acid;

1e) eliminating the excess hydrogen peroxide by adding to the solution reducing agents selected from the group consisting of pyruvic acid, pyruvic acid salts, and alkaline sulphites;

1f) preparing the enzyme Gl-7-ACA acylase from cultures of the microorganism *Escherichia coli* P-3 (p JC 200) registration number NCIMB 40433 through fermenting under aerobic conditions at a temperature of 21°–28° C., subjecting a cell mass obtained from the culture to lysis and purifying the enzyme by chromatography over DEAE resin;

1g) immobilizing the purified enzyme on an inert solid support which is insoluble in an aqueous medium and contains functional groups for forming cross-linkages with the enzymatic protein, such support being selected from the group consisting of: resins of macroreticular strongly basic polystyrene structure; phenolformaldehyde resins with secondary or tertiary amino functional groups; resins of polyacrylic structure crosslinked with divinylbenzene and functionalized with primary amino groups; polyacrylic resins with epoxide functional groups; and porous alumina impregnated with a complex a polyethylenimine and glutaraldehyde; and 1h) deacylating the glutaryl-7-aminocephalosporanic acid or its derivatives (II) by bringing the immobilized enzyme obtained in 1 g) into contact with an aqueous solution of said compound at a concentration of 10–30 g/l, at a temperature of 20°–30° C. and a pH of 7–9.

2. In the process as claimed in claim 1, the improvement consisting in that glutaraldehyde is used as a bifunctional cross-linking agent for immobilizing the enzyme.

3. A process as claimed in claim 1, wherein step 1c) is conducted by maintaining the immobilized enzyme in dispersion in the aqueous substrate solution.

4. A process as claimed in claim 1, wherein step 1c) is conducted by passing the aqueous substrate solution over the immobilized enzyme arranged in a column.

5. A process as claimed in claim 1, wherein step 1h) is conducted by maintaining the immobilized enzyme in dispersion in the aqueous substrate solution.

6. A process as claimed in claim 1, wherein step 1h) is conducted by passing the aqueous substrate solution over the immobilized enzyme arranged in a column.

7. The process according to claim 1 wherein the immobilization of the enzyme DAO is carried out by using a weakly basic resin of macroreticular polystyrene structure with a primary amino function.

8. The process according to claim 1 wherein the immobilization of the enzyme DAO is carried out by using porous alumina impregnated with a complex of polyethyleneimine and glutaraldehyde.

9. The process according to claim 1 wherein the immobilization of the enzyme Gl 7ACA acylase in carried out by using phenolformaldehyde resin with secondary or tertiary amino functional groups.

10. The process according to claim 1 wherein the immobilization of the enzyme Gl 7ACA acylase is carried out by using acrylic resin with epoxide functional groups.

11. The process according to claim 1 wherein the immobilization of the enzyme Gl 7ACA acylase is carried out by using porous alumina, impregnated with a complex of polyethyleneimine and glutaraldehyde.

* * * * *